United States Patent [19]

Roenigk et al.

[11] Patent Number: 5,141,915
[45] Date of Patent: Aug. 25, 1992

[54] DYE THERMAL TRANSFER SHEET WITH ANTI-STICK COATING

[75] Inventors: Karl F. Roenigk, Hudson, Wis.; Ronald K. Thery, New Brighton, Minn.; Verna J. LeMire, White Bear Lake, Minn.; A. Daie Otteson, West Lakeland Township, Washington County, Minn.; Gary L. Holmes, Vadnais Heights, Minn.

[73] Assignee: Minnesota Mining and Manufacturing Company, St. Paul, Minn.

[21] Appl. No.: 659,624

[22] Filed: Feb. 25, 1991

[51] Int. Cl.⁵ .................. B41M 5/035; B41M 5/26
[52] U.S. Cl. ........................... 503/227; 428/195; 428/323; 428/341; 428/421; 428/488.4; 428/500; 428/913; 428/914
[58] Field of Search ............ 428/195, 323, 341, 421, 428/488.4, 500, 913, 914; 503/227

[56] References Cited

U.S. PATENT DOCUMENTS

| 4,321,404 | 3/1982 | Williams et al. | 560/115 |
| 4,383,878 | 5/1983 | Young et al. | 156/235 |
| 4,631,232 | 12/1986 | Ikawa et al. | 428/413 |
| 4,829,050 | 5/1989 | Henzel et al. | 503/227 |

FOREIGN PATENT DOCUMENTS

| 0263478 | 10/1987 | European Pat. Off. | 428/488.4 |
| 0314348 | 10/1987 | European Pat. Off. | 503/227 |
| 0033684 | 2/1987 | Japan | 503/227 |
| 63-62790 | 3/1988 | Japan | 428/488.4 |
| 63-74687 | 4/1988 | Japan | 428/488.4 |
| 63-118296 | 5/1988 | Japan | 428/488.4 |

Primary Examiner—B. Hamilton Hess
Attorney, Agent, or Firm—Gary L. Griswold; Walter N. Kirn; Gregory A. Evearitt

[57] ABSTRACT

Thermal transfer dyesheets are disclosed containing highly efficient back-side antistick coatings. These are particularly useful in thermal dye transfer printing materials where relatively high temperatures are used in the thermal head and where dye offset from the front of one sheet to the back of an adjacent sheet is often a problem. These coatings comprise at least one polyfluorinated resin having an acrylate functionality, and at least one more resin having an acrylate functionality to provide a crosslinked matrix.

9 Claims, No Drawings

DYE THERMAL TRANSFER SHEET WITH ANTI-STICK COATING

FIELD OF THE INVENTION

This invention relates to a dye thermal transfer sheet with an anti-stick coating and more particularly, it relates to a dye thermal transfer sheet with an anti-stick coating containing polyfluorinated acrylate containing compositions.

BACKGROUND OF THE INVENTION

In recent years, thermal transfer systems have been developed to obtain prints from pictures generated electronically by a color video camera. According to one way of obtaining such prints, an electronic picture is first subjected to color separation by color filters. The respective color-separated images are then converged into electrical signals. These signals are then operated on to produce cyan, magenta and yellow electrical signals. These signals are then transmitted to a thermal printer. To obtain the print, a cyan, magenta or yellow dye-donor element (and sometimes a black element) is placed face-to-face with a dye receiving element. The two elements are then inserted between a thermal printing head and a platen roller. A line-type thermal printing head is used to apply heat from the back of the dye-donor sheet. The thermal printing head has many heating elements and is heated up sequentially in response to the cyan, magenta, or yellow signal. The process is then repeated for the other two colors. A color hard copy is thus obtained which corresponds to the original picture viewed on a screen.

A problem has existed with the use of dye-donor elements for thermal dye-transfer printing because a thin support is required in order to provide effective heat transfer. For example, when a thin polyester film is employed, it softens when heated during the printing operation and can stick to the thermal printing head. This causes intermittent rather than continuous transport across the thermal head. The dye transferred thus may not appear as a uniform area, but rather as a series of alternating light and dark bands (i.e., chatter marks). Another defect called "smiles", which are crescent shaped low density areas, is produced in the receiving element by stretch-induced folds in the dye-donor element. Another defect is produced in the receiving element when abraded or melted debris from the backing layer builds up on the thermal head and causes streaks parallel to the travel direction which may extend over the entire image area. In extreme cases, sufficient friction is often created to tear the dye-donor element during printing. It would be desirable to eliminate such problems in order to have a commercially acceptable system.

In an attempt to solve the foregoing problems, dye-donor or thermal transfer imaging sheets employed in the industry frequently make use of an anti-stick or slipping layer coated on the side distant the thermal transfer layer. Materials disclosed for anti-stick coatings include linear thermoplastic as well as crosslinked polymers, with additives of either inorganic or organic materials and/or particulate materials to enhance some aspects of performance.

EPO Publication No. 314,348 discloses a backcoat (i.e., anti-stick coating) composition for a thermal transfer dye-sheet which is representative of many such coatings used in the industry. The EPO Publication discloses an anti-stick coating containing an organic resin comprising at least one polyfunctional material have a plurality of pendant or terminal acrylic groups per molecule available for cross-linking, at least 10% by weight of the polyfunctional material having 4-8 such acrylic groups per molecule; at least one linear organic polymer soluble or partially soluble in the resin; and comprising 1-40% by weight of the resin/polymer mixture, a slip agent selected from derivatives of long chain carboxylic or phosphoric acids, long alkyl chain esters of phosphoric acids, and long alkyl chain acrylates; an antistatic agent soluble in the resin; and a solid particulate antiblocking agent less than 5 $\mu$m in diameter.

In the EPO Publication, the linear polymer is employed to impart flexibility to the cross-linked resin as well as to adjust coating viscosity and improve adhesion of the cured film to the substrate. The separate slip system consists of salts of stearic and hydroxy stearic acids; for example, lithium soaps, and salts of polyvalent metals and stearic acids (such as zinc stearate). Thicknesses recommended with these materials are on the order of 1–5 $\mu$m, preferably 1 $\mu$m. This places constraints on the antiblocking particulate size distribution.

There are several major disadvantages incurred with the use of the system disclosed by the EPO Publication. First, the slip properties of the film are imparted by mobile additives separate from the main cross-linked resin, which show a tendency to solvate dyes in the opposing layer and subsequently contaminate the printhead with the dyes. Also, the slip agents employed are salts of metals such as lithium or zinc, which are generally undesirable since these metals' ions can migrate into the opposing dye layers which may affect image properties, and into the head construction which may cause printing element failure. Additionally, talc, when used in sufficient quantities to be the main antiblocking agent, may require the thermal printer to use excessive pressure to ensure contact with the print head. This pressure can cause the inorganic particulate to abrade the printhead with time. Further, the average particle size of talc is reported as 2 $\mu$m, which can be expected to result in distributed protrusions from the antistick coating. Finally, the recommended coating thickness of from 1 to 5 $\mu$m contributes considerable thermal mass to the donor ribbon as a whole. With the standard 6 $\mu$m PET carrier film, the ribbon can be expected to require as a minimum roughly an additional 20% printing energy to deliver the required printing density. This is a serious disadvantage since the life of the costly printhead is a strong inverse function of the power expended in printing.

Fluorinated compounds have been disclosed for use in anti-stick layers and release layers. For example, EPO Publn. No. 263,478 discloses thermal transfer imaging materials with an anti-stick back layer. The transfer layer on the front surface comprises a non-flowable ink layer and an adhesive layer. An anti-stick back layer has a thickness in the range of 0.05 $\mu$m to 3 $\mu$m and contains a main component chosen from fluorine-containing surface active agents and fluorine-containing polymers. These main components are preferably mixed with heat resistant resins such as epoxy resins, silicone resins, phenolic resins, melamine resins, and polyester sulfones, and others. The fluorine containing polymers disclosed are tetrafluoroethylene-hexafluoropropylene copolymers, polychlorotrifluoroethylene, polyvinylidene fluoride, and polytetrafluoroethylene.

Japanese Kokai JP63-062790 discloses the use of a cellulose derivative mixed with a resin which can be fluorinated. No further definition of the latter resin is provided, however, and such compounds are not disclosed in the examples. The layer thickness is stated to be in the range 0.05 μm to 3 μm.

Japanese Kokai JP63-074687 discloses anti-stick back layers of thicknesses in the range 0.2 μm to 5 μm containing polyurethane fluoride as the major component.

Japanese Kokai JP63-118296 discloses thermal transfer materials with the heat transfer layer on one side of a support. On the other side of the support is a heat resistant layer which contains a perfluoroalkyl group-containing resin preferably selected from oligomers of tetrafluoroethylene and hexafluoropropylene, or from copolymers of a perfluoroalkyl group-containing vinyl monomer with (meth)acrylic acid or esters.

U.S. Pat. No. 4,631,232 discloses a heat-sensitive transferring recording material having a heat melting ink layer on one side of a substrate, and a "heat resistant conveyance improving layer" on the other side of the substrate. The conveyance improving layer comprises either UV radiation curable resins or compounds containing a perfluoroalkyl group. The former are illustrated by polyester acrylate, polyurethane acrylate, and epoxy acrylate, but no indication is made that the monomers in the curable resins may be fluorinated. The compounds containing perfluoroalkyl groups are not described as polymerizable monomers and are not UV cured; they are represented by salts or esters of perfluoroalkyl carboxylic acids, salts of perfluoroalkyl sulfonic acid, esters of perfluoroalkyl phosphoric acid, perfluoroalkyl betaine, and perfluoroalkyl trimethyl ammonium salts.

U.S. Pat. No. 4,829,050 discloses thermal transfer materials with an anti-stick back layer comprising Teflon ™ particles dispersed in a cellulose binder.

U.S. Pat. No. 4,383,878 discloses a transfer material for indicia wherein a first support base to which the indicia are applied has a release topcoat comprising a radiation-curable polyfluorinated acrylate compound and a polyethylenically unsaturated crosslinking agent.

U.S. Pat. No. 4,321,404 discloses the same radiation-curable compositions disclosed in U.S. Pat. No. 4,383,878 and presents utilities involving the controlled release of images applied to the adherent composition layers.

Although the foregoing disclosed anti-stick and release coatings containing fluorinated compounds are suitable for their intended use, improvements in such coatings are continually sought and desired by the industry for use in dye thermal transfer systems. Specifically, improvements with respect to the heat resistance, lubricity, dye impermeability, and self-cleaning properties of anti-stick coatings for thermal dye transfer sheets are constantly needed.

SUMMARY OF THE INVENTION

By the present invention, an effective dyesheet for thermal transfer printing is provided. The inventive thermal transfer dyesheet comprises a support having on one side thereof a thermal dye transfer layer and on the other side thereof an anti-stick layer comprising the polymerization reaction product of: (a) at least one polyfluorinated resin comprising an acrylate functionality; and (b) at least one ethylenically unsaturated crosslinking agent. The reaction product can also be characterized as a network polymer comprising: (a) at least one polyfluorinated resin comprising an acrylate functionality; and (b) at least one ethylenically unsaturated crosslinking agent. Preferably, about 0.5-20 wt % of the polyfluorinated resin, and most preferably about 1 wt % of the resin, is present in the anti-stick backlayer of the dyesheet. Additionally, preferably about 80-90 wt %, and most preferably about 85-95 wt %, of the ethylenically unsaturated crosslinking agent is present in the anti-stick layer.

The thermal dye transfer sheets of the present invention are very effective because of the use of the particular anti-stick compositions utilized in the dyesheets. The anti-stick layer is especially important in performance and serves to provide heat resistance to protect the heat sensitive carrier substrate and prevent distortion or loss of integrity; lubricity at printing conditions to allow for smooth slippage of the carrier under the printhead; impermeability to prevent dye and/or other material diffusion from the dye layers with subsequent possible alteration of dye layer and/or anti-stick printing performance and contamination of the printhead; and self-cleaning action while printing, preventing debris buildup at the printhead surface and subsequent streaking or other printing defects with possible printhead damage.

The thermal dye transfer materials of the present invention have been found to perform well in the printer and the anti-stick layers present in the inventive materials provide excellent barrier properties preventing dye retransfer from typical dye layers under accelerated aging conditions.

The inventive thermal dye transfer materials of the present invention employ anti-stick coatings which can be on the order of only 0.1 μm in film thickness, thus contributing negligible thermal mass to the donor ribbon and allowing for more efficient utilization of printhead energy with attendant extended printhead life. Additionally, the fluorinated anti-stick layer used in the inventive material is crosslinked into the resin matrix and thus, is relatively immobile compared with the anti-stick agents used in conventional systems. Also, the inventive materials contain no potentially corrosive ions as compared to other thermal dye transfer sheets, as disclosed in EPO Publn. No. 314,348. Finally, the use of particulate anti-blocking agents is optional, and not mandatory, in the present invention.

Other aspects and advantages of the present invention are apparent from the detailed disclosure, examples, and claims.

DETAILED DESCRIPTION OF THE INVENTION

The present invention provides a dyesheet for thermal transfer printing comprising a support having on one side thereof a thermal dye transfer layer and on the other side thereof an anti-stick layer comprising the polymerization reaction product of: (a) at least one polyfluorinated resin comprising an acrylate functionality, and (b) at least one ethylenically unsaturated crosslinking agent. The polymerization reaction of (a) and (b) is typically induced by a free-radical mechanism. The initiator for such a reaction is commonly either a thermal or photoinitiator, with the latter preferred.

Any material can be used as the support for the dye-donor element of the invention provided it is dimensionally stable and can withstand the heat of the thermal printing heads. Such materials include polyesters such as poly(ethylene terephthalate); polyamides; polycarbonates; glassine paper; condenser paper; cellulose esters such as cellulose acetate; fluorine polymers such as polyvinylidene fluoride; polyacetals; polyolefins such as polystyrene, polyethylene, polypropylene or methylpentane polymers; and polyimides such as polyimide-amides and polyether imides. The support generally has a thickness of from about 2 to about 30 μm. It may also be coated with a priming layer, if desired.

The thermal dye transfer layer of the materials of this invention may be chosen from the many formulations disclosed in the art. Preferred formulations are those making use of so-called "sublimable" dyes. The dyes are common dispersed in a polymeric binder. Typical dye classes are anthraquinone, azo, and aminostyryl, but many other dyes are disclosed in the art such as, for example, in U.S. Pat. No. 4,857,503.

The dye layer of the dye-donor element may be coated on the support or printed thereon by a printing technique such as a gravure process.

Preferably, the polyfluorinted resins comprising an acrylate functionality employed in the anti-stick coating layer of the resin invention are selected from:

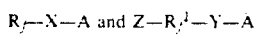

wherein:
$R_f$ is a polyfluorinated, saturated, monovalent aliphatic group which is straight, branched, or cyclic;
$R_f^1$ is a polyfluorinated, divalent, saturated aliphatic group which is straight, branched, or cyclic;
A is an acrylate or methacrylate group;
X and Y are each $C_1$ to $C_{14}$ aliphatic connecting groups which may be fluorinated with the proviso that there is an unfluorinated carbon atom connected directly to A;
Z is selected from $CF_3O-$, $C_2F_5O-$, $C_4F_9O-$, $CF_3CF(CF_3)O-$, $CF_3OCF(CF_3)O-$, or Y—A, where Y and A are as defined above.

In this context, "aliphatic" or groups may contain other covalently bonded atoms besides carbon. Included are groups where the carbon atoms are interspersed with atoms of one or more of the elements oxygen, nitrogen, and sulfur.

Preferably $R_f$ is fully fluorinated; however, desired release characteristics can be obtained with hydrogen or chlorine atoms present as substituents provided no more than one atom of either is present for every two carbons in the group. $R_f$ preferably contains 6 to 14 carbon atoms and more preferably 8 to 10 carbon atoms.

Preferably $R_f^1$ comprises highly fluorinated polyethers having units selected from at least one of the groups $-CF_2O-$, $-CF_2CF_2O-$, $-CF_2CF_2CF_2O-$, and $-CF(CF_3)CF_2O-$, and may have incorporated therein $-CF_2CF_2CF_2CF_2O-$, $-CF_2CF_2-$, and $-CF_2-$ groups. Where more than one of the groups $-CF_2O-$, $-CF_2CF_2O-$, $-CF_2CF_2CF_2O-$, and $-CF(CF_3)CF_2O-$, is selected, then these groups may be randomly distributed.

The connecting group X is preferably chosen from those with the formulae

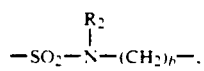

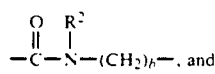

-continued

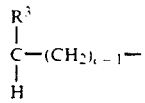

and the connecting group Y is preferably chosen from those with the formulae

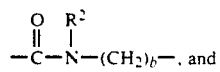

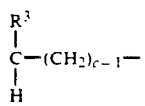

wherein:
$R^2$ is hydrogen, a lower alkyl of about 1 to 4 carbon atoms (preferably methyl or ethyl), or $-(CH_2)_d-A$ where A as is defined above,
$R^3$ is hydrogen, $CF_3$, or $CF_2Cl$;
b is 2 to 12, except that when $R^2$ is $-(CH_2)_d-A$, b is 2 or 3;
d is 2 or 3;
c is 1 to 12.

Preferably A is an ethylenically unsaturated group selected from the formulae;

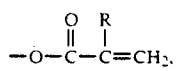

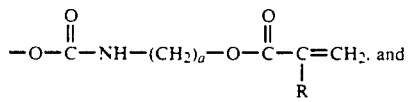

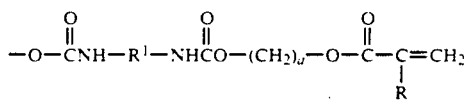

wherein:
R is hydrogen or methyl,
a is an integer having a value in the range 2 to 6; and
$R^1$ is a divalent aliphatic or cycloaliphatic group having 2 to 14 carbon atoms or an aryl group having 6 to 14 ring carbon atoms.

These fluoroacrylates may be made by the methods disclosed in U.S. Pat. No. 4,383,878.

Preferred ethylenically unsaturated functionality crosslinking agents for inclusion in the anti-stick formulations of this invention are acrylates and methacrylates. Examples include compounds with acrylic equivalent weight of about 63 to 400, and preferably about 85 to 300. Such agents are well known and are listed, for example, in U.S. Pat. Nos. 3,833,384; 3,885,964; and 4,037,021. Preferred compounds are pentaerythrytol tetraacrylate (PETA), hexamethylene diisocyanate trimer (HMDI), an adduct of HMDI and PETA, trimethylolpropane propoxylate triacrylate, and hydantoin hexacrylate. Other useful compounds are neopentylglycol ethoxylate diacrylate, pentaerythrytol triacrylate, urethane acrylates, polyester acrylates, amine acrylates, acrylated epoxides, and methoxy ether acrylates.

Examples of photopolymerization initiators which are useful in the practice of this invention include the benzoin/acetophenone classes such as benzoin, benzoin alkylethers, benzil ketals, and dialkoxyacetophenones. A preferred initiator is Irgacure TM 500 (Ciba-Geigy) which is a 50/50 mixture of benzophenone and 1-hydroxy-cyclohexylphenylketone. Another example is Irgacure TM 907 which is 2-methyl-1-[4-(methylthio)-phenyl]-2-morphalinopropanone-1. This initiator may be sensitized, for example, with isopropylthioxanthone. A further example is 1-hydroxy-1-methylethyl-phenylketone. Photoinitiators containing fluorinated aliphatic chains have been found particularly suitable and can provide high curing speeds. It is surmised that the enhanced performance of these compounds is related to their being more compatible with the fluorinated acrylates.

It is also within the scope of the invention that azo and peroxide containing materials can be utilized. Such materials are well known to those skilled in the art. Preferably, the fluoroacrylated compound should contain sufficient fluorine so that the combination of fluorinated and unfluorinated acrylates contains at least 0.05% by weight of fluorine. Owing to the limited solubility of the fluoroacrylates, which is determined by the chemical nature and length of the fluorinated relative to the non-fluorinated group, the fluoroacrylate may phase separate from the matrix acrylate, if employed, after coating. The fluoroacrylate, possessing lower surface energy, will segregate toward the coating surface, resulting in a distribution of fluorine more highly concentrated near the surface of the coating. The required weight % of fluorine to achieve functional antistick performance is thus dependent on the chemical nature of the fluorinated acrylate, its solubility and surface energy relative to the crosslinking matrix, and in addition the overall coating weight employed. For example, a longer tail fluoroacrylate will likely be less soluble in common acrylate monomers, and will likely bloom to the coating surface more efficiently than a shorter tail material. Thus, a lower total percent by weight of such a material and consequently, fluorine will be required for functionality relative to the shorter tail material. Further, with increasing coating weight, less percent by weight of the fluoroacrylate will be required for functional performance, because the fluoroacrylate tends to concentrate at or near the coating surface. If a long tail fluoroacrylate were employed which was insoluble in the matrix monomer, then for increasing coating weight, the thickness of the resulting fluoroacrylate at the coating surface would increase proportionally, conceivably to an excessive and undesirable level. This segregation of fluorine at the coating surface further enhances the impermeability and thus barrier properties of the antistick.

For coating, the components are dissolved in solvents such as methyl ethyl ketone, and polyfluorinated solvents such as DuPont Freon TM 113 and 3M FC Fluorinert TM solvents. The longer chain fluoroacrylates have limited solubility in either hydrocarbon or ketone solvents and typically the fluorinated solvents must be employed. Tertiary butyl methyl ether was found to solvate many of the perfluoroalkylether acrylates which are relatively insoluble in other non-fluorinated solvents.

It has also been found that solvent-free formulations are possible by emulsification of the fluoroacrylate in the crosslinking acrylate material. This makes it possible to use fluoroacrylates for which no good solvent can be found.

A wide range of surfactant coating aids may be added to the formulation before coating. Preferred ones in this invention are fluoroaliphatic polymeric esters.

Antistatic agents may be added to the formulations before coating to alleviate static charge buildup during handling, to improve conveyance properties in the printer, and to reduce collection of dust or other airborne particles which can result in image defects. Fluorinated antistatic agents are well known in the art and have advantages in the formulations of this invention.

Curing of the coated anti-stick layers may be carried out by methods common in the art, such as using ultraviolet light emitting lamps. Reduction of oxygen content in the curing atmosphere can be advantageous to improve surface and resistance through cure. This may be achieved by flooding the curing environment with nitrogen or other inert gases which displaces oxygen. However, this requirement can be obviated in some instances by the use of coinitiators, comonomers, and radical scavengers such as functional and non-functional amines, e.g., triethanolamine, 2-(dimethylamino)ethyl benzoate, ethyl p-(dimethylamino) benzoate, and amines with acrylate functionality or unsaturation. Radiation from the lamp may be focused or defocused onto the surface of the anti-stick layer. Focused radiation is preferable since this reduces sensitivity of the cure to oxygen levels. For temperature sensitive substrates such as polyethylene teraphthalate (PET), the infra-red radiation content of the lamp emissions may need to be absorbed by optical filters or alternatively, the substrate temperature must be controlled by heat removal.

Although the anti-stick layers used in this invention preferably do not contain particulates for the reasons given earlier in discussing the art, inert particulates may be used in certain circumstances, in particular to reduce the static and dynamic friction, and subsequently the tension required to pull the transfer ribbon through a printing device during operation. The particulates may be inorganic or organic as commonly employed in the art, including talc, zeolite, alumina, alumnosilicate, calcium carbonate, Teflon TM powder, zinc oxide, titanium oxide, magnesium oxide, silica, graphite, and others. Mean particle size should preferably be between 0.01 $\mu$m and 50 $\mu$m and more preferably between 0.01 $\mu$m and 10 $\mu$m. Depending on the hydrophilicity of particles employed, buildup of static charge may also be alleviated on the donor film by the particles, acting in the same fashion as common antistatic agents. The particulates should be present in an amount between 0.1% and about 50% or more, preferably between 1% and 20% by weight of the total resin present in the anti-stick layer. Dry coating weights of the anti-stick layers are preferably in the range 0.1 $g/m^2$ to 1.0 $g/m^2$.

EXAMPLES

Chemical abbreviations used in the examples are interpreted in the following Table.

| Class | Abbreviation | Chemical Abbreviation Description |
|---|---|---|
| | | Description |
| Fluorinated | FPEO | $(CF_2CF_2O)_x(CF_2CH_2)_yOCOCH=CH_2$ x = 7.5, y = 1.4. |

-continued

| Class | Abbreviation | Description |
|---|---|---|
| Acrylates | FPTOC | $-[(CF_2CF_2O)_m(CF_2O)_n]_x-(CF_2CH_2)_yOCOCH=CH_2$ $m/n = 3.28, x = 5.8, y = 1.5.$ |
| | FPTHF | $-(CF_2CF_2CF_2CF_2O)_x-(C_3F_6CH_2)_yOCOCH=CH_2$ $x = 8.4, y = 1.6$ |
| | FPPG | $-(CF_2CF(CF_3)O)_x-CF_2CH(CF_3)OCOCH=CH_2$ $x = 5.8$ |
| | FX-13 | $C_8F_{17}SO_2N(CH_2CH_3)CH_2CH_2OCOCH=CH_2$ (3M product) |
| | FBEE | $C_4F_8OC_2F_4OCF_2CH_2OCOCH=CH_2$ |
| | KRYTOX | $C_3F_7O(CF(CF_3)CF_2O)_xCF(CF_3)CH_2OCOCH=CH_2$ $x = 10.3.$ |
| | FOA | $C-F_{15}CH_2OCOCH=CH_2$ (3M product) |
| | FCY | $C_6F_{11}CH_2OCOCH=CH_2$ (fluorocyclohexyl) |
| | FCYM | $C_6F_{11}CH_2OCOCH(CH_3)=CH_2$ (fluorocyclohexyl) |
| | FC550 | $CF_3O(CF_2CF_2O)_xCF_2CH_2OCOCH, x = 5.8.$ |
| | FPEMO | $-[(CF_2CF_2O)_m(CF_2O)_n]_x-(CF_2CH_2)_y-(OCOCH=CH_2)_z$ $m/n = 0.8, x = 12.6, y \geq 1.95, z \geq 1.95.$ |
| Acrylates | PETA | pentaerythrytol tetraacrylate |
| | PET3A | pentaerythrytol triacrylate |
| | HMDI | hexamethylene diisocyanate trimer (3 functional isocyanate) |
| | HMDITA-7 | adduct of pentaerythrytol triacrylate and singly reacted HMDI with $HOCH_2CH_2OCOCH=CH_2$, i.e. $(HMDI)-PET_3A)_2-OCH_2CH_2OCOCH=CH_2$ |
| | HHA | hydantoin hexacrylate (3M product) |
| | Photomer TM 4160 | neopentylglycol ethoxylate diacrylate (Henkel) |
| | Photomer TM 4072 | trimethylolpropane propoxylate triacrylate (Henkel) |
| Initiator | Irgacure TM 500 | 50/50 blend of benzophenone and 1-hydroxy cyclohexylphenylketone (CIBA-GEIGY) |
| Surfactant | FC-430 | fluoroaliphatic polymeric esters (3M product) |
| | FC-431 | fluoroaliphatic polymeric esters (3M product) |
| Solvents | MEK | methyl ethyl ketone |
| | FC-86 | fluorocarbon (3M Fluorinert TM liquid) |
| | Freon TM 113 | 1,1,2-trichloro-1,2,2-trifluoroethane (TF grade, DuPont) |
| Substrates | PET | poly(ethylene terephthalate) |

EXAMPLE 1

Four formulations were made and tested as follows:

TABLE 1

| Component | % of solids for solution # | | | |
|---|---|---|---|---|
| | 1 | 2 | 3 | 4 |
| FC-550 | 8.92 | 8.95 | 4.67 | 4.68 |
| FC-430 | 0.34 | 0 | 0.36 | 0 |
| Photomer TM 4072 | 84.74 | 85.03 | 88.70 | 87.01 |
| Irgacure TM 500 | 6.0 | 6.02 | 6.28 | 6.3 |
| | 100 | 100 | 100 | 100 |

Solutions were prepared with these solids compositions at 8% total solids in Freon TM 113. Solutions were then applied to a 5.7 μm PET substrate used for donor sheets by slot-die coating at dry coating weights of 0.3 and 0.6 g/m². Dried coatings were cured continuously on the substrate at 20 fpm (6.1 m/min) using a 200 W/in (80 W/cm) UV lamp system. A standard 300 dot/inch (11.8 dots/mm) printhead was employed with a backup platen hardness of 55 Shore Gauge A and 1.6 pounds/-lineal inch (0.29 kg/cm) engagement pressure. Maximum temperatures at the printhead in these tests were estimated from pyrometer measurements to approach 300° C. All coatings performed well in the printer with smooth passage and quiet operation.

EXAMPLE 2

All formulations referred to herein are described in Table 2. Coating and curing was carried out using a RPC UV processing unit with nitrogen inerting. This curing unit contained two medium pressure mercury lamps; for a nominal 300 W/in (120 W/cm) operation each lamp was estimated to emit the following power at the indicated peak wavelengths: 11.1 W at 254 nm, 10.3 W at 313 nm, and 17.5 W at 365 nm. Curing was typically carried out at 200 W/in (80 W/cm) using one or both lamps, with one or two passes through the machine at speeds from 20 ft/min to 50 ft/min (6.1 m/min to 15.25 m/min). Coatings were made using a #4 Meyer rod (~10 μm wet thickness), with one and two passes through the curing unit at 25 ft/min (7.6 m/min). One pass at these conditions yielded a total dosage of roughly 200 mj/cm² using a Dynachem integrating radiometer (λ=360 nm+/−25 nm). These cured samples were then aged against actual dye coated layers.

Aging was carried out in dry (50° C.) and wet (40° C., 90% RH) ovens for up to 2 weeks by layering dye and anti-stick coatings face to face under a pressure between 0.1 to 0.2 pounds/inch² (7 to 14 g/cm²).

TABLE 2

| Formulation Description. | | |
|---|---|---|
| ID# | Components | Amt (g) |
| 1 | FPEO | 1.22 |
| | HMDITA-7 | 1.66 |
| | Irgacure TM 500 | 0.1 |
| | FC-430 | 0.03 |
| | MEK | 25.43 |
| | Freon TM 113 | 49.73 |
| 2 | FPEO | 1.23 |
| | HMDITA-7 | 2.53 |
| | Irgacure TM 500 | 0.13 |
| | FC-430 | 0.02 |
| | MEK | 31.9 |
| | Freon TM 113 | 62.5 |
| 3 | FPEO | 0.65 |

TABLE 2-continued

Formulation Description

| | | |
|---|---|---|
| | HMDITA-7 | 2.57 |
| | Irgacure ™ 500 | 0.15 |
| | FC-430 | 0.02 |
| | MEK | 27.6 |
| | Freon ™ 113 | 54.4 |
| 4 | (HMDI)₃(LTM)₂PETA | 2.11 |
| | Irgacure ™ 500 | 0.05 |
| | FC-430 | 0.02 |
| | FC-86 | 52.84 |
| 5 | FC-550 | 1.25 |
| | HMDITA-7 | 2.52 |
| | Irgacure ™ 500 | 0.10 |
| | FC-430 | 0.02 |
| | MEK | 32.97 |
| | Freon ™ 113 | 62.6 |
| 6 | HMDITA-7 | 6.64 |
| | FX-13 | 2.02 |
| | Irgacure ™ 500 | 0.13 |
| | FC-430 | 0.02 |
| | MEK | 200 |
| 7 | FPPG | 0.5 |
| | HMDITA-7 | 1.5 |
| | Irgacure ™ 500 | 0.04 |
| | FC-430 | 0.04 |
| | MEK | 17.45 |
| | Freon ™ 113 | 33.68 |
| 8 | FPTHF | 0.53 |
| | HMDITA-7 | 1.52 |
| | Irgacure ™ 500 | 0.05 |
| | FC-430 | 0.015 |
| | MEK | 17.78 |
| | Freon ™ 113 | 34 |
| 9 | FPTOC | 0.51 |
| | HMDITA-7 | 1.51 |
| | Irgacure ™ 500 | 0.04 |
| | FC-430 | 0.01 |
| | MEK | 17.40 |
| | Freon ™ 113 | 33.50 |
| 10 | (HMDI)₃-(LTM)₂-PETA | 1.01 |
| | Irgacure ™ 500 | 0.03 |
| | Freon ™ 113 | 25.25 |
| 11 | FOA | 1.0 |
| | HMDITA-7 | 4.0 |
| | Irgacure ™ 500 | 0.07 |
| | FC-430 | 0.02 |
| | MEK | 41.41 |
| | Freon ™ 113 | 83.76 |
| 12 | (HMDI)₃-(LTM)₃ | 2.04 |
| | Irgacure ™ 500 | 0.03 |
| | FC-430 | 0.01 |
| | Freon ™ 113 | 51.9 |
| 13 | FCY | 0.27 |
| | HMDITA-7 | 1.08 |
| | Irgacure ™ 500 | 0.04 |
| | FC-430 | 0.01 |
| | MEK | 11.6 |
| | Freon ™ 113 | 24.6 |
| 14 | (HMDI)₃-(LTM)₂-PETA | 1.5 |
| | Irgacure ™ 500 | 0.05 |
| | FC-430 | 0.01 |
| | MEK | 37.8 |
| 15 | FCYM | 0.51 |
| | HMDITA-7 | 2.04 |
| | Irgacure ™ 500 | 0.05 |
| | FC-430 | 0.01 |
| | MEK | 21.1 |
| | Freon ™ 113 | 44.5 |
| 16 | (HMDI)₃-(LTM)₂-PETA | 2.08 |
| | Irgacure ™ 500 | 0.02 |
| | FC-430 | 0.01 |
| | Freon ™ 113 | 52.7 |
| 17 | FC-550 | 0.26 |
| | HMDITA-7 | 1.08 |
| | Irgacure ™ 500 | 0.05 |
| | FC-430 | 0.01 |
| | MEK | 10.9 |
| | Freon ™ 113 | 23.10 |
| 18 | (HMDI)₃-LTM-PETA | 1.51 |
| | Irgacure ™ 500 | 0.04 |
| | FC-430 | 0.01 |
| | MEK | 37.64 |
| 19 | FC-550 | 0.25 |
| | HMDITA-7 | 4.77 |
| | Irgacure ™ 500 | 0.06 |
| | FC-430 | 0.01 |
| | MEK | 42.0 |
| | Freon ™ 113 | 84.50 |
| 20 | (HMDI)₃-(C₇F₁₅)-(PETA)₂ | 1.5 |
| | Irgacure ™ 500 | 0.04 |
| | FC-430 | 0.01 |
| | MEK | 38.1 |
| 21 | FPEO | 0.12 |
| | HMDITA-7 | 2.37 |
| | Irgacure ™ 500 | 0.04 |
| | FC-430 | 0.01 |
| | MEK | 20.70 |
| | Freon ™ 113 | 41.90 |
| 22 | FC-550 | 0.30 |
| | HHA | 1.21 |
| | Irgacure ™ 500 | .04 |
| | FC-430 | 0.01 |
| | MEK | 12.36 |
| | Freon ™ 113 | 25.4 |
| 23 | FC-550 | 0.19 |
| | Photomer ™ 4160 | 1.72 |
| | Irgacure ™ 500 | 0.04 |
| | FC-430 | 0.01 |
| | Freon ™ 113 | 48.3 |
| 24 | FPEO | 0.30 |
| | HHA | 1.21 |
| | Irgacure ™ 500 | 0.04 |
| | FC-430 | 0.01 |
| | MEK | 12.4 |
| | Freon ™ 113 | 25.3 |
| 25 | FC-550 | 0.26 |
| | Photomer ™ 4072 | 2.47 |
| | Irgacure ™ 500 | 0.08 |
| | FC-430 | 0.01 |
| | Freon ™ 113 | 70.1 |
| 26 | FPEO | 0.4 |
| | PET₃A | 1.22 |
| | Irgacure ™ 500 | 0.04 |
| | FC-430 | 0.01 |
| | MEK | 17 |
| | Freon ™ 113 | 34 |
| 27 | FPEMO | 0.5 |
| | PETA | 0.04 |
| | MEK | 12.9 |

Donor dye layer formulations used in these examples.
DYE COLOR.

| Yellow | Components | % of solids |
|---|---|---|
| | PTS #2 | 11.9 |
| | Dye A | 11.9 |
| | Nippon Kayaku MQ-452 | 23.7 |
| | Geon 178 PVC | 39.5 |
| | Vitel PE 200 | 1.98 |
| | Troysol CD1 Dispersant | 11.1 |
| | | 100 |

| Magenta | Components | % of solids |
|---|---|---|
| | AQ-1 | 23.9 |
| | Mitsibushi Kasei HSR-31 | 23.9 |
| | Geon 178 PVC | 27.9 |
| | Vitel PE200 | 1.99 |
| | ODA/AA Copolymer | 11.2 |
| | Troysol CD1 | 11.2 |
| | | 100 |

| Cyan | Components | % of solids |
|---|---|---|
| | Foron Brilliant Blue | 23.4 |
| | Dye B | 23.4 |
| | Geon 178 PVC | 31.2 |
| | ODA/AA Copolymer | 6.54 |
| | Vitel PE 200 | 3.12 |
| | UVINUL N539 (BASF) | 12.5 |
| | | 100 |

The dyes in these formulations were as follows:

| Yellow | |
|---|---|
| TPS #2 | N-(1-Anthraquinonyl)-2-ethylhexamide |
| Dye A | N-(4-Hydroxyanthraquinon-1-yl)-p-toluenesulfonamide |
| Nippon Kayaku MQ-452 | 1-Butyl-3-cyano-4-methyl-5-(3,4-dichloroazobenzene-6-hydroxypyrid-2-one |
| Magenta | |
| Mitsubishi Kasei HSR-31 | p-tricyanovinyl-N-butyl-N-(2-phenylethyl)-aniline |
| AQ-1 | N-(4-Amino-3-methoxyanthraquinon-1-yl)-p-Toluenesulfonamide |
| Cyan | |
| Dye B | 1,4-bis-(1-Methylhexylamino)-5,8-dihydroxyanthraquinone |
| Foron Brilliant Blue | Propanedinitrile [2-[[4-(dihexylamino)-2-methylphenyl]methylene]benzo[b]thien-3-(2H-ylidene)]-5,5-dioxide |

RESULTS

Results are shown in Table 3, corresponding to two-pass cures at approximately 400 mj/cm² dose as measured by a radiometer integrating between 330 and 400 nm. All materials provided generally quite printer operation. A standard 300 dot/inch (11.8 dots/mm) printhead was employed with a backup platen hardness of 55 Shore Gauge A and 1.6 pounds/lineal inch (0.29 kg/cm) engagement pressure. Maximum temperatures at the printhead in these tests were estimated from pyrometer measurements to approach 300° C. Printer noise as a result of the "stick-slip" phenomenon was noted at specified voltages as indicated in Table 3.

TABLE 3

Performance of antistick layers aged against dye donor layer.

| | | Days Aged before Observable Dye Transfer for | | | | | |
|---|---|---|---|---|---|---|---|
| | Max volts | Wet Oven (40° C, 90% RH) | | | Dry Oven (50° C.) | | |
| Formula # | without noise | Y | M | C | Y | M | C |
| 1 | 17.5 | 3 | * | 7 | 7 | * | * |
| 2 | 20 | 7 | * | * | * | * | 3 |
| 3 | 20 | 7 | 4 | 7 | 4 | * | 4 |
| 4 | 20 | 1 | 1 | 1 | 1 | 1 | 1 |
| 5 | 20 | 7 | 7 | 7 | 3 | * | 1 |
| 6 | 16.5 | — | — | — | — | — | — |
| 7 | 20 | — | — | — | — | — | — |
| 8 | 20 | 7 | 7 | 7 | 4 | 1 | 1 |
| 9 | 17.5 | — | — | — | — | — | — |
| 10 | 20 | 1 | 1 | 1 | 3 | 1 | 1 |
| 11 | 17.5 | — | — | — | — | — | — |
| 12 | 20 | 1 | * | 1 | 1 | 1 | 1 |
| 13 | 20 | — | — | — | 1 | * | 1 |
| 14 | 20 | — | — | — | — | — | — |
| 15 | 20 | * | * | 1 | 1 | * | 1 |
| 16 | 20 | 1 | 1 | 1 | 1 | 1 | 1 |
| 17 | 20 | — | — | — | — | — | — |
| 18 | — | — | — | — | — | — | — |
| 19 | 20 | — | — | — | — | — | — |
| 20 | 20 | — | — | — | — | — | — |
| 21 | 20 | * | * | * | * | * | 7 |
| 22 | 20 | — | — | — | — | — | — |
| 23 | 20 | 3 | 3 | 1 | 1 | 1 | 1 |
| 24 | 20 | 7 | 7 | 7 | 7 | 7 | 7 |
| 25 | 20 | * | * | * | 1 | 3 | 7 |
| 26 | 20 | * | * | 7 | 1 | * | * |
| 27 | 20 | — | — | — | 1 | 1 | 1 |

"—" indicates data not taken.
"*" indicates better than one week without transfer

EXAMPLE 3

This example illustrates the effect of 1) fluoroacrylate level, and 2) coating weight on surface cure and resultant unreacted fluoroacrylate which can be of concern if the backcoated material is stored in wound-up form before coating the dye layers on the other surfaces.

Coatings from Example 1 were prepared as described and wound up on cylindrical cores for storage. Samples were removed from these cores and coated with the cyan formulation described in Example 2, at 4% solids in a 20%/35%/45% tetrahydrofuran, methyl-ethyl ketone/cyclohexanone solvent system. Coatings were applied to the opposite side of the antistick after it was in roll form. A #8 wire wound Meyer rod was used to yield dry coating weights near 1 g/m². Contamination of the face side was indicated by poor wettability of the cyan coating after application, with various degrees of wetting behavior being observed depending on the fluoroacrylate coating parameters. For example, severe dewetting implies extensive beading up of the coating, moderate implies that dewetting is not extensive but scattered, and slight implies that no beading of solution is observed, although nonuniformities in the coating may be observable due to poor wetting. Results were as follows:

| Antistick solution # | Degree of dewetting for antistick coating weight of: | |
|---|---|---|
| | 0.3 g/m² | 0.6 g/m² |
| 1 | severe | severe |
| 3 | slight | moderate |
| 4 | slight | severe |

Results indicate that surface transferrable unreacted fluoroacrylate is reduced at the lower coating weight and with the reduced fluoroacrylate levels for the 0.3 g/m² antistick coating weight.

EXAMPLE 4

This example illustrates the effect of the fluoroacrylate tail length on printer performance. Two fluoroacrylates were used: FBEE and KRYTOX. These two compounds were prepared at varying levels of % of solids in the following formulation, keeping the ratio of fluoroacrylate to FC-430 constant at 26.24, and the ratio of Photomer 4072 to Irgacure ™ 500 constant at 14.12.

TABLE 4

| | % of solids for formulation # | | | | | | | | | |
|---|---|---|---|---|---|---|---|---|---|---|
| Component | 1 | 2 | 3 | 4 | 5 | 6 | 7 | 8 | 9 | 10 |
| FBEE | 8.93 | 20 | 30 | 40 | 50 | — | — | — | — | — |
| KRYTOX | — | — | — | — | — | 0.5 | 1 | 2 | 5 | 8.93 |

TABLE 4-continued

| Component | % of solids for formulation # | | | | | | | | | |
|---|---|---|---|---|---|---|---|---|---|---|
| | 1 | 2 | 3 | 4 | 5 | 6 | 7 | 8 | 9 | 10 |
| FC-550 | 0.34 | 0.762 | 1.14 | 1.52 | 1.91 | 0.019 | 0.038 | 0.076 | 0.19 | 0.34 |
| Photomer 4072 | 84.7 | 74 | 64.3 | 54.6 | 44.9 | 92.9 | 92.4 | 91.5 | 88.5 | 84.7 |
| Irgacure TM 500 | 6.0 | 5.2 | 4.6 | 3.87 | 3.18 | 6.58 | 6.54 | 6.48 | 6.27 | 6.0 |
| | 100 | 100 | 100 | 100 | 100 | 100 | 100 | 100 | 100 | 100 |

Solutions were prepared based on these solids contents at 3% solids in Freon TM 113 and coated on 5.7 μm PET with a #4 wire wound rod yielding a dry coating weight of about 0.5 g/m². Curing was carried out at 30 fpm (9.15 m/min) with two 200 W/inch (80 W/cm) lamps giving roughly 200 mj/cm² dose.

Additional samples of formulations 1 and 2 above were coated with a #8 Meyer rod, yielding a coating weight of roughly 1 g/m². These samples and samples from formulation 3 were exposed to a double cure of 400 mj/cm² (2 passes through curing unit). Printer results are presented in Table 5 below.

The results clearly indicate the importance of tail length in providing sufficient lubricity to the antistick, with a lesser percentage of solids being required of the longer tail fluoroacrylate (F-acrylate) in order to achieve satisfactory printer performance.

TABLE 5

| F-acrylate | Solution # | % F-acrylate in solids | Cure (mj/cm²) | Wire Rod # | Printer Test |
|---|---|---|---|---|---|
| FBLE | 1 | 8.92 | 200 | 4 | Fail |
| | | | 400 | .. | .. |
| | | | 200 | 8 | .. |
| | | | 400 | .. | .. |
| | 2 | 20 | 200 | 4 | Fail |
| | | | 400 | 4 | .. |
| | | | 200 | 8 | .. |
| | | | 400 | .. | .. |
| | 3 | 30 | 200 | 4 | .. |
| | | | 400 | .. | .. |
| | | | 200 | 8 | .. |
| | | | 400 | .. | .. |
| | 4 | 40 | 200 | 4 | .. |
| | 5 | 50 | 200 | .. | Pass |
| Krytox | 6 | 0.5 | 200 | 4 | Fail |
| | 7 | 1 | .. | .. | Pass |
| | 8 | 2 | .. | .. | .. |
| | 9 | 5 | .. | .. | .. |
| | 10 | 8.92 | .. | .. | .. |

EXAMPLE 5

In an attempt to further improve surface cure, a soluble fluorinated photoinitiator was tested. This initiator was found to be soluble in the FC550 acrylate. The initiator was synthesized by combination of fluorinated polypropylene glycol acylfluoride (FPPG) and the Merck initiator Darocure 2959. Its chemical formula, confirmed by NMR, is as follows:

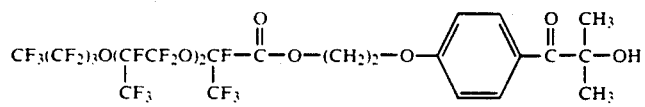

This will be referred to as FD2959. Its photoactivity was studied in a UV visible spectrophotometer, and compared to absorbance of the original Darocure 2959 initiator. The characteristic absorbance is preserved in the 250-400 nm range. Photoactivity of this compound is further confirmed by differential photocalorimetry (DPC) studies. The following table illustrates the dramatic effect on the enthalpy of reaction and overall reaction efficiency 30% increase), by adding FD2959 at a level of 1% relative to the FC550 acrylate, where the control formulation is identical to Solution #1, in Example 1.

DPC results of control formulation and control plus FD2959 at 1% of the FC550 level.

| Formulation | Enthalpy of Reaction (J/g) |
|---|---|
| Control | 211 |
| Control + FD2959 | 266 |

Tests were then carried out using this novel initiator with the control formulation to determine its effect on surface cure and reduction of contamination. The control formulation was prepared along with three additional formulations having FD2959 at 1%, 5% and 10% of FC-550. This was then coated at 3% solids with a #4 Meyer rod, yielding dry coating weights of about 0.5 g/m². The control formulation was cured at three total dosages of 100, 150, and 300 mj/cm² as measured by a Dynachem integrating radiometer. The other three formulations with FD2959 were cured at a single dose of 100 mj/cm² (30 fpm {9.15 m/min} with single 200 W/in {80 W/cm} lamp). These coated antisticks were then aged against clean Teijin at 50° C. and roughly 0.2 psi {0.014 kg/cm²} for one hour. The aged Teijin was then coated with the same cyan formulation as described in the previous example, by handspread, and checked for dewetting. Results from this study are presented in the following table.

The effect of addition of FD2959 at only 1% of the FC-550 is dramatic in reducing contamination. Further addition appears to worsen contamination, although at a reduced level compared to the control. Thus, the effect of a soluble photinitiator is apparently to improve surface cure and reduce transferrable unreacted fluoroacrylate.

Contamination study with control formulation and added FD2959.

TABLE 6

| Formulation | Dose (mj/cm²) | Dewetting |
|---|---|---|
| Control | 100 | Severe |
| Control | 150 | Severe |
| Control | 300 | Severe |
| Control + 1% FD2959 | 100 | Slight |
| Control + 5% FD2959 | 100 | Moderate |
| Control + 10% FD2959 | 100 | Moderate |

Also interesting to note from the Table 6 is that increased cure did not reduce apparent dewetting for the control formulation, indicating that the photoinitiator is exhausted predominantly in the matrix acrylate phase. This is confirmed in other DPS studies showing virtually no solubilization of the Irgacure 500 initiator in FC-550, and stresses the need for attention to the solubility of the photoinitiator.

EXAMPLE 6

This example demonstrates the effect of particulate additions to the formulations. Hydrophobic fumed silica R972 from Degussa Corporation having a primary particle size of 0.016 μm, was added to the formulation as described below at levels of 1, 5, and 10% of total solids.

TABLE 7

| Component | % OF SOLIDS | | | | PHR | | | |
|---|---|---|---|---|---|---|---|---|
| | Control | #1 | #2 | #3 | Control | #1 | #2 | #3 |
| FC550 | 9.30 | 9.21 | 8.84 | 8.37 | 10.62 | 10.62 | 10.62 | 10.62 |
| P4072 | 87.60 | 86.72 | 83.22 | 78.84 | 100.00 | 100.00 | 100.00 | 100.00 |
| IRG 500 | 2.80 | 2.77 | 2.66 | 2.52 | 3.20 | 3.20 | 3.20 | 3.20 |
| FC430 | 0.30 | 0.30 | 0.29 | 0.27 | 0.34 | 0.34 | 0.34 | 0.34 |
| R972 SILICA | 0.00 | 1.00 | 5.00 | 10.00 | 0.00 | 1.15 | 6.02 | 12.68 |
| TOTAL | 100 | 100 | 100 | 100 | | | | |

Solutions of these formulations were prepared at 3% solids in Freon TM 113, and coated using a #4 wire wound rod, yielding coatings with roughly 0.5 g/m² coating weight. Samples were cured with a single RPC UV lamp at 200 W/inch (80 W/cm) and at speeds of 20 to 50 fpm (6.1 m/min to 15.25 m/min), corresponding to 140 mj/cm² to 60 mj/cm² dosage as measured by the Dynachem integrating radiometer. Samples of the control formulation, and that formulation with 5% and 10% levels of silica passed quietly through the printer with head temperatures near 270° C. The case at 1% silica resulted in stick-slip behavior in the printhead, detectable by chatter noise. Lubricity is improved at the higher silica loadings where interfacial contact is reduced, but reduced at the 1% level.

EXAMPLE 7

This example will illustrate the preparation of fluoroacrylated compositions in a solventless fashion with coating and curing to obtain functional antistick materials. The following formulation was prepared.

TABLE 8

| Component | PHR | % of Solids |
|---|---|---|
| FC-550 | 10 | 8.55 |
| Photomer 4072 | 100 | 85.47 |
| Irgacure TM 500 | 7 | 5.98 |
| | | 100 |

A solution of the matrix acrylte Photomer 4072 and the photoinitiator Irgacure TM 500 was first prepared in proportions described above. Addition of the fluoroacrylate was then made, and the entire solution was then hand shaken to moderately disperse the fluoroacrylate, which readily emulsifies once added. Thereafter, a Branson Model 350 Sonifier was employed having a 20 KHZ frequency operation, and using amplitude setting of 5 at 50% cycle. The ultrasonic probe was immersed in the dispersion and allowed to sonicate for 5 minutes to achieve more complete dispersion of the fluoroacrylate in the matrix phase. Droplet sizes resulting from similar sonication procedures were measured in the 50-100 mm range, and the resulting emulsion was observed to remain stable for several days when left standing at room temperature. The emulsion was then blade coated to four coating weights measured at 0.15, 0.24, 0.52, and 0.93 g/m². Coatings were cured in an RPC unit with two 200 W/in lamps at 50 fpm yielding a dosage near 100 mj/cm² for a single pass through the UV curing unit. All coatings performed well in printer tests with quiet and smooth operation, with head temperatures approaching 300° C., and operating parameters as described in Example 1.

TABLE 9

| Coating weight emulsion (g/m²) | Dosage (mj/cm²) | Printer Results |
|---|---|---|
| 0.93 | 100 | Pass |
| 0.52 | 100 | Pass |
| 0.52 | 200 | Pass |
| 0.24 | 200 | Pass |
| 0.15 | 200 | Pass |

Reasonable modifications and variations are possible from the foregoing disclosure without departing from either the spirit or scope of the present invention as defined by the claims.

What is claimed is:

1. A thermal transfer dyesheet comprising a support having on one side thereof a thermal dye transfer layer and on the other side thereof an anti-stick layer comprising the reaction product of:
   a) at least one polyfluorinated resin comprising an acrylate functionality; and
   b) at least one ethylenically unsaturated crosslinking agent.

2. A thermal transfer dyesheet as recited in claim 1 wherein said antistick layer further comprises a coating-aid surfactant.

3. A thermal transfer dyesheet as recited in claim 1 wherein said antistick layer further comprises inert particulate material of particle size in the range 0.01 μm to 10 μm.

4. A thermal transfer dyesheet as recited in claim 1 wherein said polyfluorinated resin is selected from the group consisting of polyfluorinated alkyl acrylates and methacrylates, and poly(fluorooxyalkalene)acrylates and methacrylates.

5. A thermal transfer dyesheet as recited in claim 1 wherein said polyfluorinated resin is selected from the group consisting of:

wherein:
$R_f$ is a polyfluorinated, saturated monovalent, aliphatic radical;
$R_f^1$ is a polyfluorinated, divalent saturated, aliphatic radical;
A is an acrylate or methacrylate radical;

X and Y are each $C_1$ to $C_{14}$ aliphatic connecting groups which may be fluorinated with the proviso that there is an unfluorinated carbon atom attached directly to A; and Z is selected from the group consisting of $CF_3O—$, $C_2F_5O—$, $C_4F_9O—$, $CF_3CF(CF_3)O—$, and $—Y—A$ wherein Y and A are each as defined above.

6. A thermal transfer dyesheet material as recited in claim 5 wherein:

$R_f$ contains from 6 to 14 carbon atoms and is perfluorinated; or $R_f^1$ is selected from the group consisting of $—CF_2O—$, $—CF_2CF_2O—$, $—CF_2CF_2CF_2O—$, and $—CF(CF_3)CF_2O—$;

X is chosen from the group consisting of:

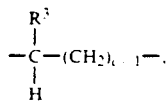

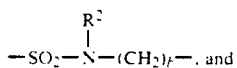

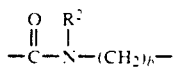

Y is chosen from the group consisting of:

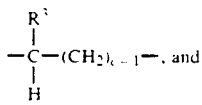

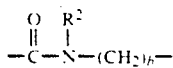

wherein:

$R^2$ is hydrogen, a lower alkyl of about 1 to 4 carbon atoms, or $—(CH_2)_d—A$ where $R^3$ is hydrogen, $CF_3$, or $CF_2Cl$;

d is 2 or 3, c is 1 to 12; and

A is selected from the group consisting of:

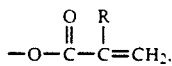

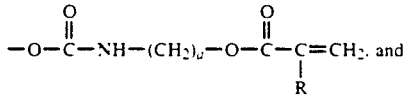

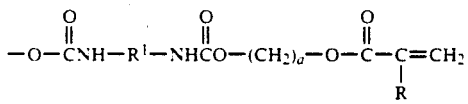

wherein:

R is hydrogen or methyl, a is an integer having a value in the range 2 to 6, and $R^1$ is a divalent aliphatic or cycloaliphatic group having 2 to 14 carbon atoms or an aryl group having 6 to 14 carbon atoms.

7. A thermal transfer dyesheet as recited in claim 1 wherein said crosslinking agent has an acrylic equivalent weight in the range 63 to 400.

8. A thermal transfer dyesheet as recited in claim 1 wherein said crosslinking agent is selected from the group consisting of pentaerythrytol tetraacrylate; hexamethylene diisocyanate trimer; an adduct of hexamethylene diisocyanate trimer and pentaerythrytol; hydantoin hexacrylate; neopentylglycol ethoxylate diacrylate; trimethylolpropane propoxylate triacrylate; and pentaerythrytol triacrylate.

9. A thermal transfer dyesheet as recited in claim 1 wherein said anti-stick layer has a dry coating weight in the range 0.1 $g/m^2$ to 1.0 $g/m^2$.

* * * * *